United States Patent [19]
Cole et al.

[11] Patent Number: 5,514,104
[45] Date of Patent: May 7, 1996

[54] ABSORBENT ARTICLES

[75] Inventors: Robert Cole, Jackson; Daniel Formosa, Montvale; Thomas J. Helmestetter, Piscataway; Rory Holmes, Princeton; Stephen Russak, Fort Lee, all of N.J.; Robert Salome, Newtown, Pa.; Beth Stern, Cranbury; Robert L. Sun, Succasunna, both of N.J.; Tucker Viemeister; Stacy A. Walsh, both of New York, N.Y.; Jennifer R. Worringer, East Windsor, N.J.

[73] Assignee: McNeil-PPC, Inc., Milltown, N.J.

[21] Appl. No.: 296,995

[22] Filed: Aug. 26, 1994

Related U.S. Application Data

[63] Continuation of Ser. No. 21,290, Feb. 22, 1993, abandoned.

[51] Int. Cl.$^6$ ............................ A61F 13/15; A61F 13/20
[52] U.S. Cl. .................. 604/366; 604/358; 604/365; 604/369; 604/378; 604/380; 604/382; 604/384; 604/385.1
[58] Field of Search ................... 604/358, 368–369, 604/378–385.1, 365–366

[56] References Cited

U.S. PATENT DOCUMENTS

| | | | |
|---|---|---|---|
| 2,952,259 | 9/1960 | Burgeni | 604/380 |
| 3,665,922 | 5/1972 | Skora . | |
| 3,993,820 | 11/1976 | Repke . | |
| 4,259,387 | 3/1981 | Mesek . | |
| 4,578,070 | 3/1986 | Holtman . | |
| 4,605,404 | 8/1986 | Sneider . | |
| 4,642,110 | 2/1987 | Dudek | 604/385.1 |
| 4,685,914 | 8/1987 | Holtman | 604/369 |
| 4,738,675 | 4/1988 | Buckley et al. . | |
| 4,798,603 | 1/1989 | Meyer et al. . | |
| 4,865,597 | 9/1989 | Mason, Jr. et al. | 604/385.1 |
| 4,886,697 | 12/1989 | Perdelwitz, Jr. et al. . | |
| 4,892,532 | 1/1990 | Boman . | |
| 4,908,026 | 3/1990 | Sukiennik et al. . | |
| 4,917,697 | 4/1990 | Osborn, III et al. . | |
| 5,037,409 | 8/1991 | Chen et al. . | |
| 5,135,521 | 8/1992 | Luleri et al. | 604/383 |
| 5,171,302 | 12/1992 | Buell | 604/369 |
| 5,374,260 | 12/1994 | Lemay et al. | 604/379 |
| 5,387,206 | 2/1995 | Valentine et al. | 604/358 |

FOREIGN PATENT DOCUMENTS

| | | |
|---|---|---|
| 0021662 | 1/1981 | European Pat. Off. . |
| 0301491 | 2/1989 | European Pat. Off. . |
| 2089214 | 6/1982 | United Kingdom ................ 604/380 |
| 2266645 | 11/1993 | United Kingdom . |
| WO91/14415 | 10/1991 | WIPO . |

OTHER PUBLICATIONS

EPO Search Report, Appln. 94102626.2, Aug. 1, 1995.

*Primary Examiner*—Randall L. Green
*Assistant Examiner*—P. Zuttarelli

[57] ABSTRACT

The present invention provides improvements in absorbent products, but is particularly useful with urinary incontinence pads. An embossed pattern on the bottom layer of the double layer absorbent core construction improves the removal of urine or other fluids from the discharge zone to be ready for next void. One or more V-shaped notches cut at both ends of the pad provides the ergonomic fit of the pad to reduce the inevitable stiffness. The sides are designed as a flap which curves during the sealing process and provide natural curved flaps which form a soft gasket cushion and yields extra leak protection in the crotch area.

38 Claims, 8 Drawing Sheets

ABSORBENT ARTICLES

This is a continuation of application Ser. No. 08/021,290, filed Feb. 22, 1993, now abandoned.

The present invention relates to articles for absorbing body fluids. More particularly the present invention relates to pads for absorbing menstrual fluids and/or urine.

BACKGROUND OF THE INVENTION

There are numerous shapes, styles and constructions of absorbent articles designed to absorb and retain menstrual fluid or urine, the latter being used to alleviate urinary incontinence. These pads are generally placed against the perineal area of a subject and are held in place by the crotch portion of an undergarment. However, certain products have an integral panty, while others use straps or belts as affixing devices. Finally, certain absorbent products cover a larger area, e.g., infant and adult incontinent diapers. Thus, for purposes of the present invention, terms such as absorbent article or pad are meant to encompass all of these types of devices.

The use of a composite structure comprised of cellulosic fibers and superabsorbent powder as an absorbent for diapers, catamenial pads, incontinence pads, and other absorbent articles is well known. One problem associated with the application of this composite is its limited liquid transport capacity, caused by the so called "gel block" phenomena. When liquid is initially absorbed the superabsorbent swells and forms a gel, however, this gel inhibits further liquid absorption within the absorbent structure. This problem is particularly severe after long wearing with a thin layer construction that has a very small cross section or critical mass for wicking to take place after liquid is introduced.

Prior attempts have been made to reduce or eliminate the gel-block phenomenon, For example, U.S. Pat. No. 4,798,603 claims an absorbent article with a liquid-permeable transport layer placed between the cover and the absorbent core. The transport layer is made of a material which is less hydrophilic than the absorbent core and which has an effective average pore size that is smaller than the cover layer pore size. U.S. Pat. No. 4,892,532 discloses an absorbent article with a thin spun-bonded hydrophobic cover and a hydrophobic melt-bonded fabric layer between the cover and the absorbent core. The hydrophobic melt-bonded layer has a higher basis weight than the cover fabric. U.S. Pat. No. 4,908,026 discloses an absorbent article with a cover that has perforations arranged in the center of the product. A "flow zone control" layer is placed between the cover and the absorbent core in the area under the cover's perforations. U.S. Pat. No. 5,037,409 discloses an absorbent article with a "flow-modulating" layer between the absorbent and the cover. This flow-modulating layer consists essentially of hydrophilic meltblown fibers. U.S. Pat. No. 4,578,070 discloses an absorbent product with a first layer of synthetic resilient fibers united to a second layer with a higher capillary pressure than the first layer. The difference in capillary pressure causes fluid to be preferentially drawn into the second layer. The united layers are corrugated to form a stable structure.

None of these transfer layers, nor any combination of absorbent structures known in the prior art is fully effective against gel blocking. Moreover, many of the proposed solutions add unduly complex combinations of materials and/or structural features to the absorbent product making them less efficient to manufacture and more expensive. It therefore would be desirable to provide an absorbent structure that eliminated gel blocking. Accordingly, it is an object of the present invention to provide an absorbent article that comprises a modified absorbent core that channels fluid toward unwetted portions of absorbent material.

Additionally, it has been found that certain absorbent products tend to exude absorbed fluids when pressed between the legs of the wearer. Although attempts have been made to create absorbent materials that retain absorbed fluid under pressure, much of the exudate flows from the peripheral edge of the pad. It is therefore a further object of the present invention to provide absorbent articles that reduce or eliminate leakage along their edges.

Along with the above-described improvements in materials and articles for absorbing body fluids and efficiently distributing them within absorbent articles, the overall geometry of absorbent structures has been constantly refined. The shape of an absorbent article has two important aspects. First, shape largely dictates the comfort with which an absorbent article may be worn. Secondly, shape also contributes to absorbent performance by enabling the absorbent materials to remain in contact with the body or otherwise disposed in an appropriate position. For these reasons, it is desirable to eliminate phenomena such as twisting or "roping," folding along non-conformal axes, crushing, sliding, and other movement that detracts from absorbency, causes discomfort or causes the exudation of absorbed fluid. It is therefore an object of the present invention to provide improvements in the geometry of absorbent products. In particular it is an object of this invention to provide pads that will exhibit improved conformance with the perineal region of a wearer when used as either a catamenial pad or female urinary incontinence appliance.

SUMMARY OF THE INVENTION

These and other objectives are met by providing absorbent articles containing an absorbent structure for rapidly spreading absorbed liquid that overcomes the above-described gel blocking problem. The present invention provides improved fluid transport by embossing the bottom layer of an absorbent core that contains a superabsorbent polymer. The high density channels created by such embossing continuously spread liquid a further distance. Certain preferred embodiments also includes a "C-fold" structure with tissue layer wrapped inside the absorbent core for additional wicking function; the opening of the C-folding forms a pocket when fluid strikes the pad.

The present invention also provides absorbent articles that comprise a liquid impervious backing that is most preferably a foam. The backing not only functions as a liquid barrier, but also most preferably forms a peripheral gasketing edge that prevents leakage. In a preferred embodiment, the backing material comprises a thermoformed three dimensional shell and is covered with a coverstock of fusible non-woven, spunbond, or knitted fabrics.

Finally, the present invention also discloses improvements in the geometry of absorbent articles that are preferably used in conjunction with the above described absorbent structures, but which are also useful with any form of absorbent material. Generally, it has now been found that by removing a section of absorbent material, e.g., a V-shaped notch, from either end of an absorbent article, improvements in fit, comfort and performance will be obtained. In a preferred embodiment, a single V-shaped notch is formed at an end of a pad. In other preferred embodiments, multiple notches, scalloped notches or slits are formed in the absorbent material. In certain embodiments, a continuous sheet of material covers the notched or cut section to limit its range of motion and provide improved fit characteristics. In a most preferred embodiment, the continuous sheet of material is disposed on the body facing side of the absorbent material.

DETAILED DESCRIPTION OF THE INVENTION

Figure 1:
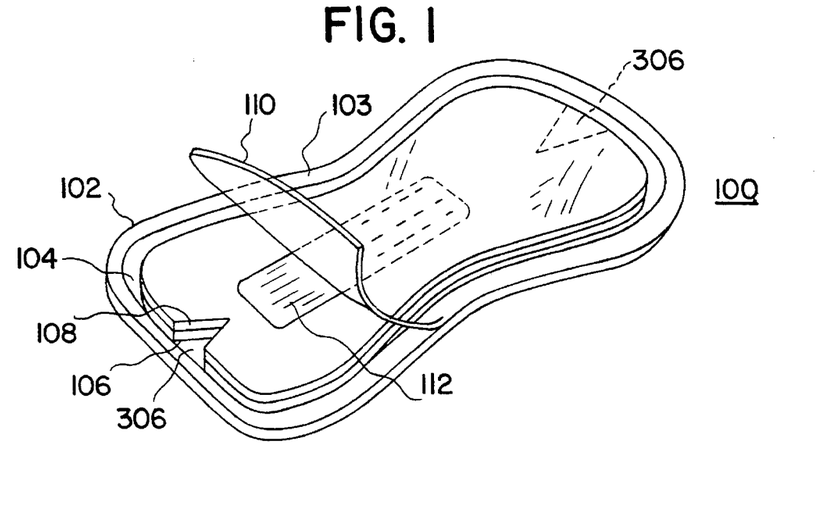
FIG. 1 is a perspective view of a preferred embodiment of an absorbent article made in accordance with the present invention.

FIG. 1 illustrates a perspective view of a preferred embodiment of an absorbent article made in accordance with the present invention, i.e., a urinary pad 100, which preferably comprises a backing material 102, an absorbent core 104 and a cover layer 110. The backing material 102 is preferably comprised of polyethylene-containing foam and is about 0.025" thick. Most preferably, the foam is a thermoformable foam with a density of about six pounds per cubic foot, such as that supplied by Voltek Co (Lawrence, Me.). The shell is shaped into a predetermined three dimensional shell by vacuum forming to give depth between ⅛" to ½". The backing material also can be a plastic film or a laminated structure with fabric and film or a resin embedded fabric that is preferably either a non-woven or woven material. The film material can be a homopolymer, a copolymer of blends of various densities or different structures such as low density, superlow density, high density, linear or branched polyethylene or propylene polymers. These films also can be a copolymer of polyethylene with ethyl-vinyl acetate or acrylates or methacrylates, such as methyl acrylate, ethyl acrylate, butyl acrylate, hexyl acrylate, octyl acrylate, their higher homolog and other geometric or optical isomers and all corresponding methacrylates.

In a first aspect of the present invention, the backing material 102 is formed to include a gasketing edge 103 that most preferably extends around the peripheral edge of the absorbent article. Portions of the gasketing edge will contact the inner thigh or other portions of the wearer's body and will form a seal therewith. The seal will substantially reduce or eliminate the edge leaking described above without causing additional discomfort or binding.

The backing material 102 contains a two piece bonded absorbent core 104 comprising a bottom layer 106 and a top layer 108. In a preferred embodiment, each of the layers 106, 108 is comprised of a cellulosic material such as wood fibers and are adhesive bonded for pad integrity for extended wearing. In a preferred embodiment, the top layer 108 contains an absorbent material comprised of a pulp structure stabilized by bonding with thermoplastic synthetic wood pulp so as to prevent collapse when liquid is introduced. A structure comprised solely of pulp would fall apart. Most preferably, the lower layer 106 is impregnated with superabsorbent powder and, in accordance with the present invention has a pattern of areas of alternating densities embossed into its surface. The absorbent core 104 formed by the lower layer 106 and the upper layer 108 will define a body-facing side and a garment facing side, and the lower layer 106 is preferably disposed on the garment facing side.

In the preferred embodiment illustrated, a cover layer 110 is disposed on the body facing side of the absorbent core 104 and substantially covers it. Preferably, the cover layer 110 is attached to the backing material 102, most preferably by heat bonding. The cover layer 110 is most preferably a non-woven fabric made from polypropylene spunbond fibers or with bicomponent fusible fibers.

In addition to the above-described components, certain embodiments of the present invention will also include a transfer layer 112 that is disposed on the body-facing side of the absorbent core 104; the cover layer 110 also overlies the transfer layer 112. The transfer layer 112 may cover only a portion of the top layer 108 and is most preferably comprised of a non-woven of polyester fiber, sold by Scott Paper Company of Philadelphia, Penna.

Another aspect of the present invention is visible in FIG. 1 and is discussed in further detail below. By providing notches 306 in the posterior and anterior ends of the absorbent core, improved conformance to the wearer's body is achieved and improved fluid absorption and retention results.

Figure 2:
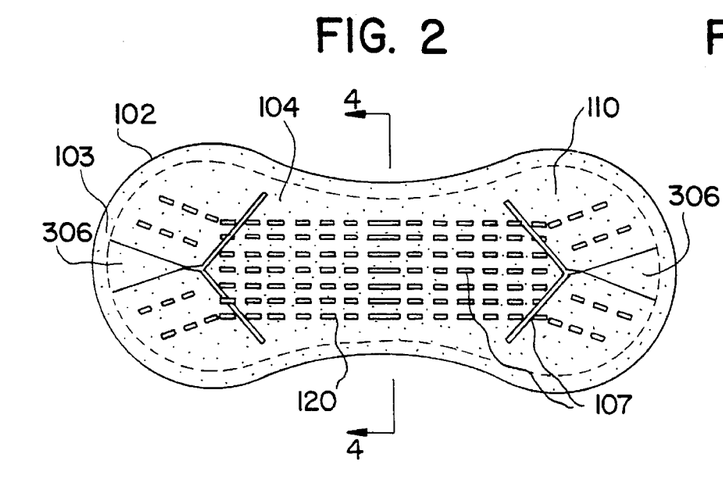
FIG. 2 is a top plan view of the absorbent article shown in FIG. 1.

Referring now to FIG. 2, there is shown a top plan view of the absorbent article 100 shown in FIG. 1. Certain features described with reference to FIG. 1 have been omitted for clarity, while other features are illustrated in this view that were omitted from FIG. 1. Thus, as seen in FIG. 2, one aspect of the present invention is illustrated by the parallel phantom lines depicting the embossed pattern 120 in the bottom layer 106 of the absorbent core 104. As explained in further detail below, the embossed pattern can be formed in a number of different configurations. However, the embossed pattern 120 should generally be laid out so as to channel fluids across the body facing surface of the absorbent article 100 to enhance absorption. Also visible in FIG. 2 are the longitudinal fold line 107 and angle fold lines 107 that are formed in the body facing side of the top layer 108 in certain embodiments.

As explained above, the bottom layer 106 preferably contains superabsorbent powder randomly placed in pulp fibers and bonded with low melting thermoplastic short fibers. The embossing 120 of the bottom layer 106 creates areas of varying density that conduct liquid across the entire surface. Thus, the compressed embossing lines 120 reduce the gel block effect which inhibits absorbed liquid from further travel.

Figure 3:
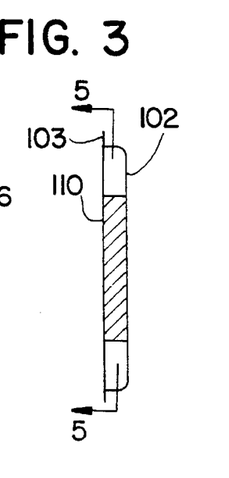
FIG. 3 is an end view of an absorbent article such as that shown in FIG. 1.
Figure 5A:
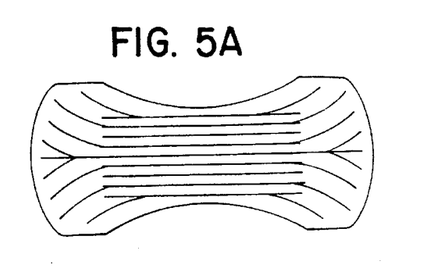
FIGS. 5A–5E are top plan views taken along line 5—5 in FIG. 3, illustrating different embossing patterns placed on the lower layer of the absorbent core.
Figure 5B:
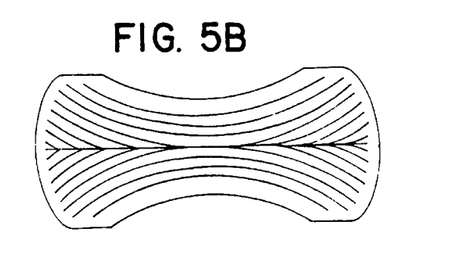

Referring now to FIGS. 5A–5E, there are shown numerous variations to the pattern of embossed lines 120 visible in phantom in FIG. 2. The views shown in FIGS. 5A–5E are all taken along line 5—5 of FIG. 3 and thus may be thought of as a top view with the top layer 108 peeled off. The embossed lines 120 may be substantially straight, as in FIGS. 5A, 5C–5E, or they may be curved, as seen in FIG. 5B. The lines may be parallel, or they may intersect, or a series of intersecting parallel lines can be formed.

Figure 5C:
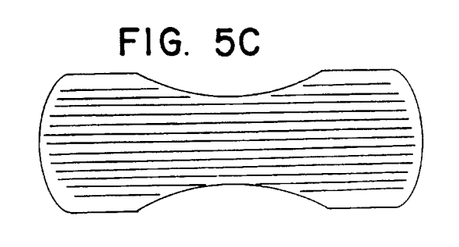
Figure 5D:
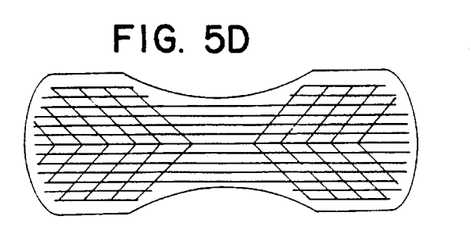
Figure 5E:
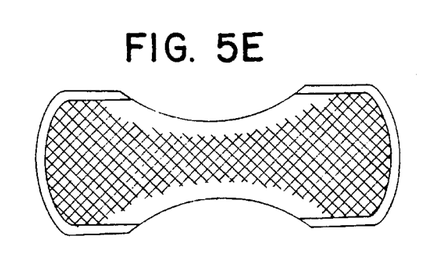

One of the advantages of the products of this invention is their ability to utilize a greater proportion of the absorbent material contained in the absorbent core of the pad by wicking fluid along greater distances of the pad. In order to measure wicking distance, fifty grams of saline solution were added to the center of the pads to be tested from a separatory funnel. The solution was added at a rate of 6 ml/sec. The maximum distance along which the solution travelled (wicking distance) was measured and recorded for three samples of each of the following embodiments. It was found that 83% more wicking distance can be achieved using the embossments disclosed, as seen in Table I:

| Pattern | Distance, in | % Increased |
| --- | --- | --- |
| Not Embossed | 4.75 | 0 |
| FIG. 5A | 8.70 | 83.16 |
| FIG. 5B | 8.17 | 72.00 |
| FIG. 5C | 8.50 | 78.95 |
| FIG. 5D | 8.26 | 73.89 |
| FIG. 5E | 8.67 | 82.53 |

Figure 4:
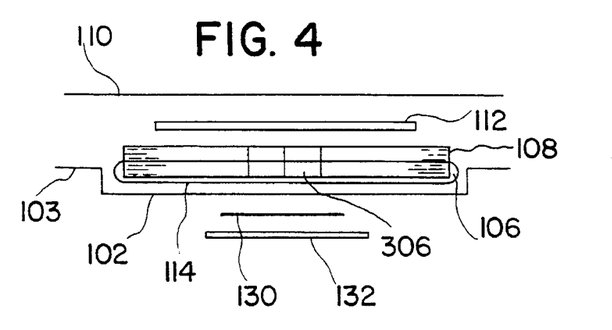
FIG. 4 is an exploded cross-sectional view of the absorbent article shown in FIGS. 1–3, taken along line 4—4 in FIG. 2.

Thus, as seen in the exploded end view of FIG. 4, the components of the pad described above include the absorbent core, comprised of a bottom layer 106 and a top layer 108 that are disposed inside a backing material 102 and covered by a cover layer 110. A transfer layer 112 is placed between the cover layer 110 and the body facing side of the top layer 108. Typically, an adhesive strip 130 is applied to the garment facing side of the backing material 102 to adhere the absorbent article to a garment. the adhesive is typically covered with a release paper 132 prior to use.

Also visible in FIG. 4 is a tissue overwrap layer 114 that may be included in certain embodiments. Most preferably, the tissue layer 114 is C-folded around the bottom layer 106 as shown. A C-folded construction is known in the art and is disclosed for example in U.S. Pat. No. 4,654,040—Luceri, which is assigned to the assignee of the present invention and is incorporated herein by reference. The C-fold may terminate along the longitudinal centerline of the bottom layer 206, thereby forming another fluid conducting channel. In other words, the center portion of the tissue layer 114 is disposed on the garment facing side, while the ends are disposed between the layers 106, 108.

Figure 6:
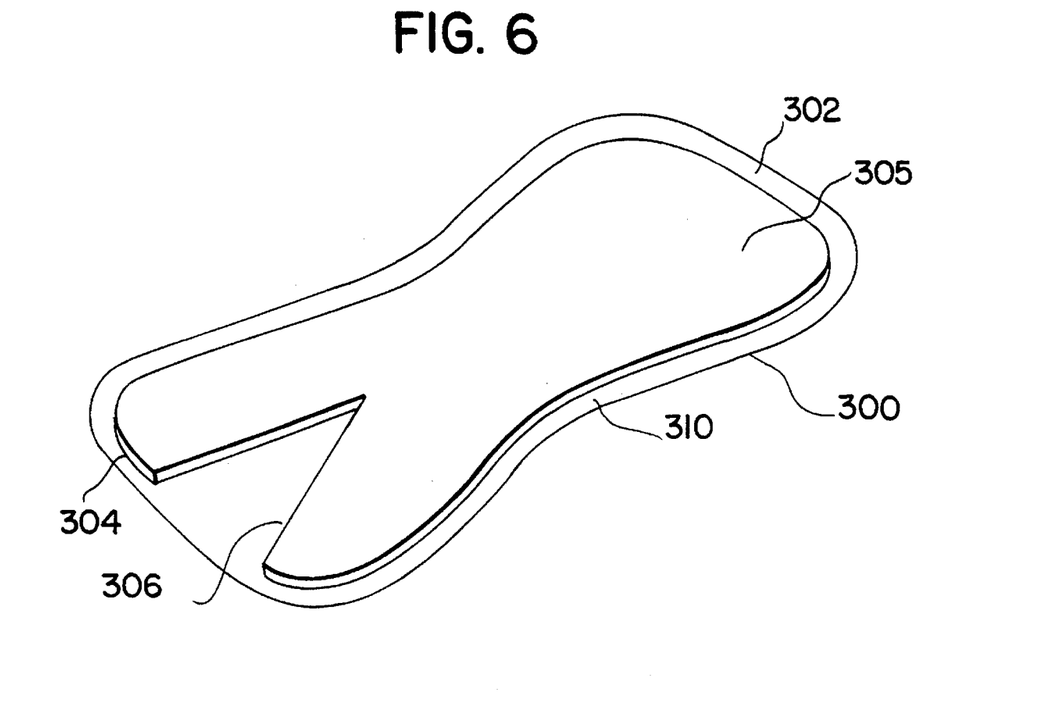
FIG. 6 is a top plan view of another preferred embodiment of the absorbent article of this invention.

Referring now to FIG. 6, there is shown a first embodiment of the improved geometries disclosed by the present invention. As explained in further detail below, although the geometries disclosed herein are useful with the improved absorbent structures described above with reference to FIGS. 1–5, it will be understood that these geometries are useful with almost any absorbent pad construction, from simple layers of cotton wadding to complex structures formed of layers of dissimilar materials.

Thus, as seen in FIG. 6, an absorbent article 300 can be constructed in the form of a catamenial pad or female incontinence appliance or similar absorbent article that has an anterior end 302 and a posterior end 304. In the embodiment shown, the posterior end 304 includes a "V"-shaped notch 306, although a similar notch could be placed in the anterior end 302 or both ends 302,304. The pad 300 is preferably formed of an absorbent layer 305 that includes a garment facing side and a body-facing side. A cover layer 310 is disposed over one of these sides. It should be noted that in the embodiment shown in FIG. 6 the cover layer 310 is disposed on the body facing side and is not cut away in the region of the notch 306 that has been cut in the absorbing layer 305.

Figure 7A:
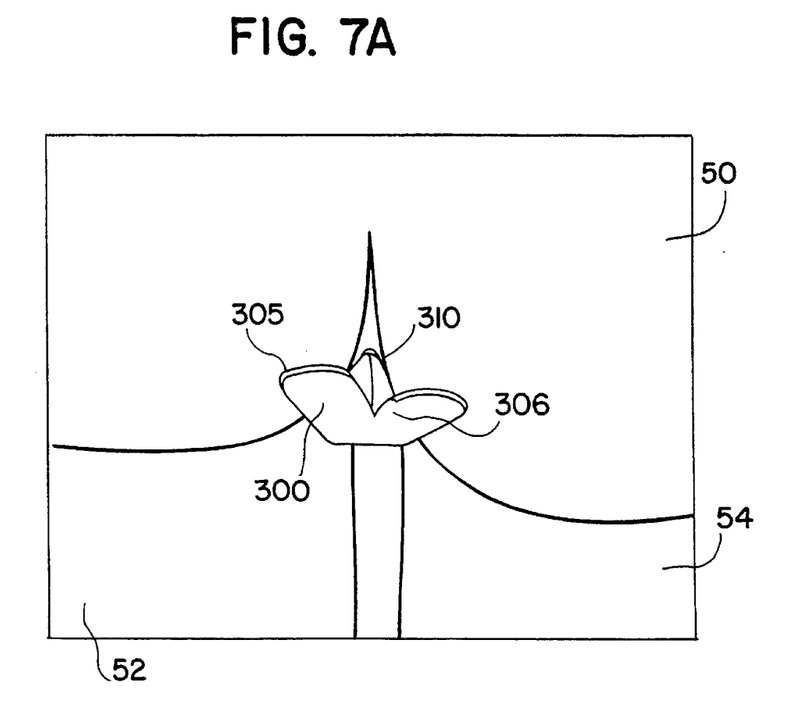
FIGS. 7A and 7B are views of a preferred embodiment of the absorbent article of this invention shown as worn on the body of a user as the legs move in a walking action.
Figure 7B:
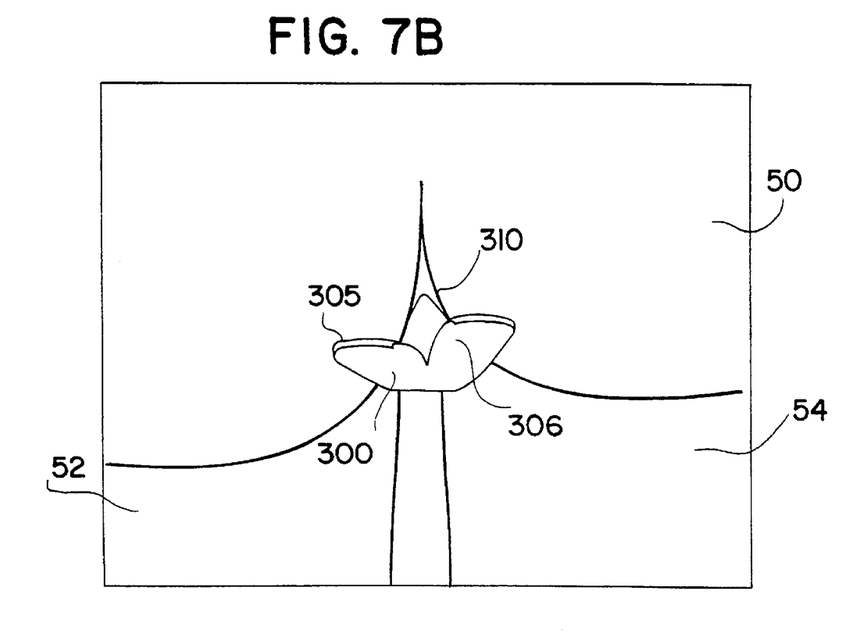

The present invention thus provides both improved wearer comfort and improved conformance to the wearer's body. Thus, as illustrated in FIGS. 7A–7B, when the pad 300 described above with reference to FIG. 6 is worn by a person 50, the V-shaped notch 306 creates an added degree of freedom across the substantially planar surface of the pad 300. This is seen by first referring to FIG. 7A, where the subject's left leg 52 is shown in a stepping forward position, while the right leg 54 is relatively behind the left leg 52. Those familiar with human anatomy and locomotion will appreciate that in this leg position, the buttocks will be in the relative position shown. The pad 300 of the present invention can accommodate for this body movement, however, as illustrated. The V-shaped notch 306 permits the relative movement of the two separate portions of the absorbent layer 305 that are disposed on the anterior portion of the perineal area and between the buttocks. However, despite the movement of the absorbent layer 305, the cover layer 310 remains in conformance with the body 50 of the wearer. Additionally, the cover layer 310 controls the amount of movement the absorbent layer 305 may undergo. Referring now to FIG. 7B it can therefore be seen that upon the shifting of the left leg 52 backward and the right leg 54 forward, the relative positions of the portion of the absorbent layer 305 adjacent the V-shaped notch 306 are reversed. The overall effect is that the pad 300 made in accordance with FIG. 6 permits the absorbent article to follow the movement with the body during walking.

Figure 8:
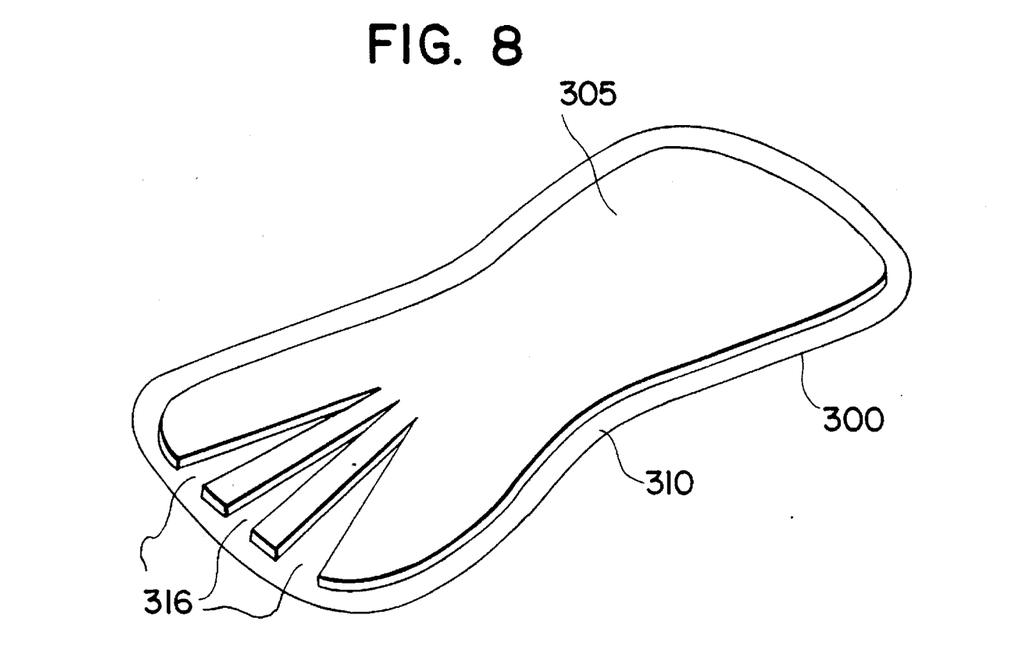
FIG. 8 is a top plan view of a preferred embodiment of the absorbent article of this invention.

It will be appreciated that the embodiment described above with reference to FIG. 6 is susceptible to numerous variations. Referring to FIG. 8, there is shown an embodiment of a pad 300 substantially as shown and described above that is comprised of an absorbent layer 305 and a body-facing cover layer 310. In the embodiment shown, a plurality of notches 316 are cut into the anterior portion of the pad 300. These notches 316 result in a plurality of partially independent portions of the absorbent layer 305 that extend from the pad 300 and are interconnected by the cover layer 310. Although three notches 316 are illustrated, it will be understood that nearly any number may be used, depending upon the size and stiffness of the pad 300 and the ultimate application. In any embodiment, pads made in accordance with the present invention will provide improved dynamic and static conformance, as explained above.

Figure 9:
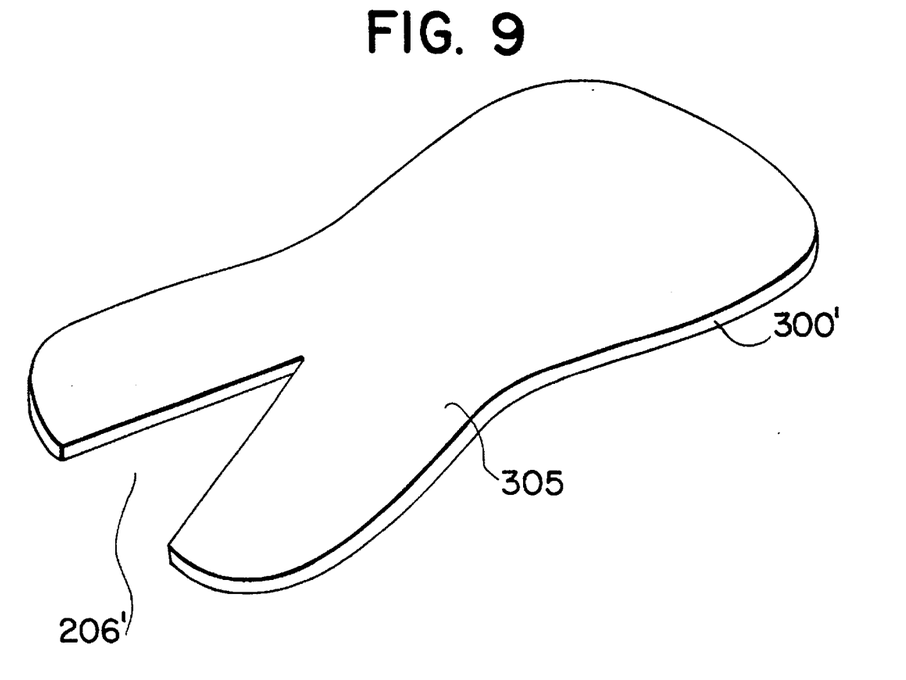
FIG. 9 is a top plan view of a preferred embodiment of the absorbent article of this invention.

Another embodiment of the present invention is illustrated in FIG. 9. The embodiments described above all included a cover layer 310, shown for example in FIG. 6. However, as seen in FIG. 9 this layer may be omitted and a pad 300' with a single notch 206' devoid of material may be constructed. Those of ordinary skill will appreciate that the embodiment shown in FIG. 9 will be relatively more flexible than those shown in FIGS. 6 and 8, and will also permit a greater range of motion. Commensurate with such changes, however, will be potential improvements in wearer comfort.

Figure 10:
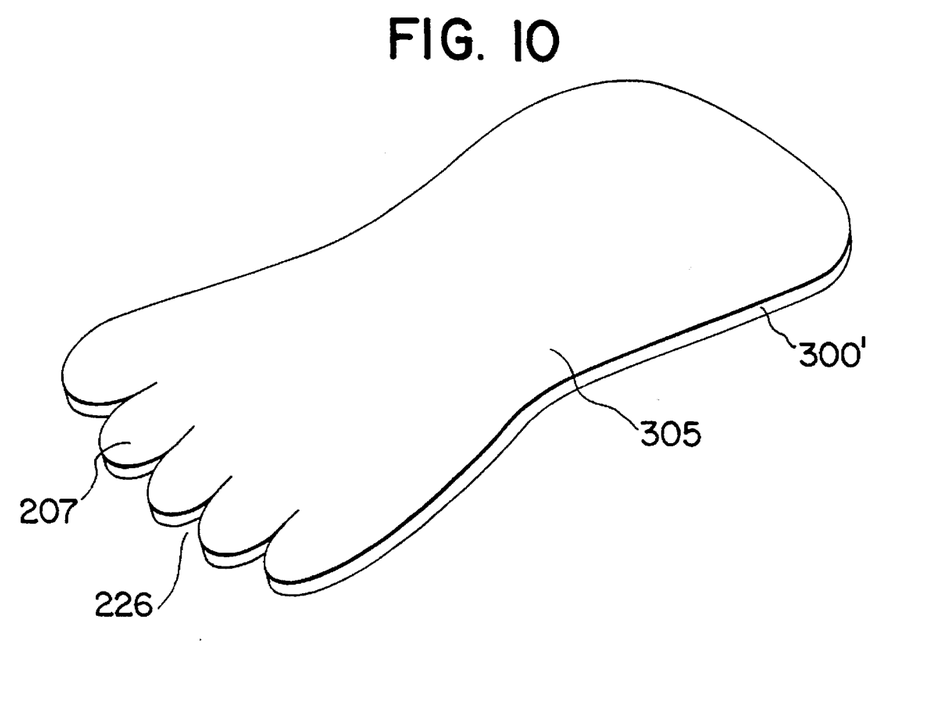
FIG. 10 is a top plan view of a preferred embodiment of the absorbent article of this invention.

Certain embodiments of the present invention may also be constructed that utilize notches that are other than V-shaped. For example, as seen in FIG. 10, curved or scalloped fingers 207 can be created in the absorbent layer by appropriately shaped scalloped notches 226. The curved extensions formed will exhibit different characteristics than those described above, and depending upon their length, width, and the material of the absorbent layer 305, can be either more conformable or less conformable than those described above. Moreover, these notches 226 can also be attached by an additional layer of material if desired, such as the cover layer 310 described with reference to FIGS. 6 and 8.

Figure 11:
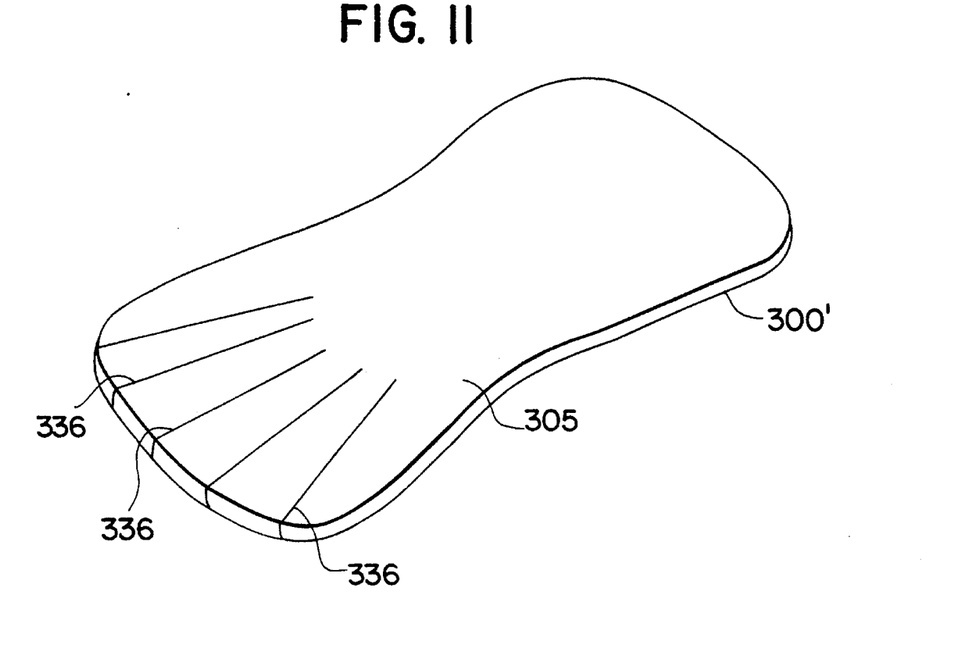
FIG. 11 is a top plan view of a preferred embodiment of the absorbent article of this invention.

In the limit, a notch that removes a minimum amount of material is essentially a slit. Thus, as shown in FIG. 11, a series of slits 336 may be used to form a series of independent portions in the absorbent layer 305 of a pad 300' substantially as described above with reference to FIGS. 9–10. In certain embodiments, it will be desirable to connect these independent portions by spanning the slits 326 with an additional layer of material that has not been slit such as the cover layer 310 described with reference to FIGS. 6 and 8. A explained above, the flexural characteristics of the portions of the absorbent material between the slits 336 will depend upon the width and length of the slits and on the properties of the absorbent material itself.

Figure 12:
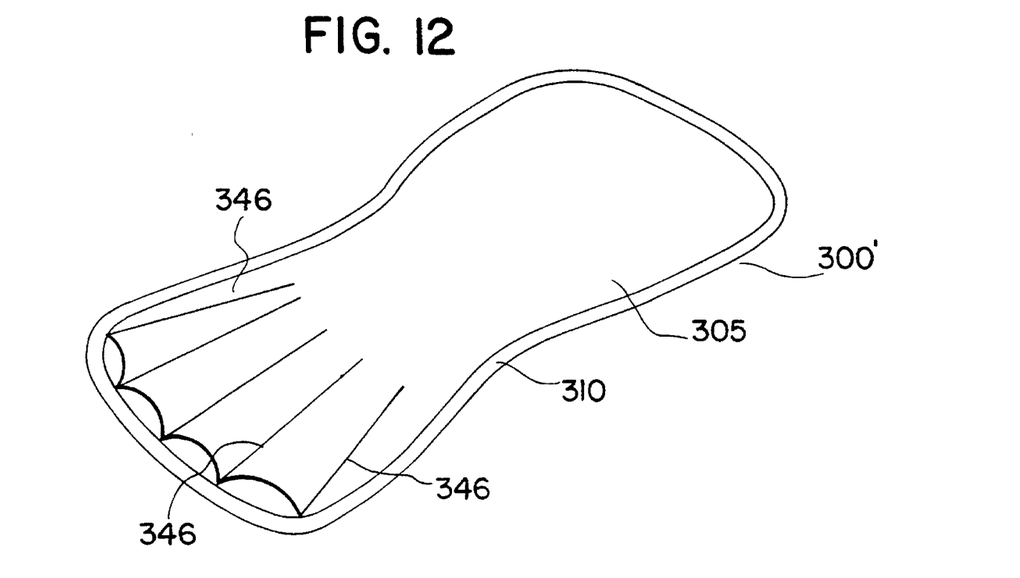
FIG. 12 is a top plan view of a preferred embodiment of the absorbent article of this invention.

Still another alternative embodiment of the present invention is shown in FIG. 12. In this embodiment, the flexural characteristics of an end of a pad 300' are influenced by a series of stitches or embossed lines 346. These form areas along which the pad 300' will naturally tend to fold or crease. These stitches or embossments 346 may be made through the entire absorbent structure, or only through an absorbent layer 305 that is then overlaid with a continuous sheet of material 310 that most preferably forms a body-facing layer.

Thus, in general terms the present invention discloses the concept of creating at least two distinct portions at an end of an absorbent article that are divided by a modified portion. In the case of a notch, the modified portion consists of removing material, and in certain embodiments, providing a cover layer. In any embodiment, however, the flexural characteristics are altered.

The notches placed in the products of this invention may be in the shape of a square, a reverse V, a half moon, a rectanle and/or any combinations of the foregoing. V-shaped notches may be defined by a combination of the cutting distance "d" as set forth in FIG. 13, which describes the depth of the cut of the notch; and of the cutting angle, as set forth in FIG. 13. Preferably, d is between about 0.5" and about 2" and the angle is between about 30° and about 90°. More preferably, d should be between about 1" and about 2", or more deep, and should be narrower, i.e., between about 30° and about 45°. The deeper the cut and the narrower the cutting angle, the more comfortable and better fitting the product. Of course, d should not be so long that the notch interferes with the absorbent capacity of the pad. Furthermore, should not be so wide that it would detract from absorbent capacity.

In any embodiment, however, the pads described herein will exhibit improved conformability, as explained above with reference to FIGS. 7A–7B. More particularly, it should be noted that in the case of anterior notches or slits the back section of feminine hygiene pads has significant influence on comfort and performance of the products. The pad needs to conform to the body, and move with the body. The present invention allows the pad to conform and move with the body, improving performance and comfort. The use of the present invention at the back of the pad provides several advantages: (1) it allows the two halves of the pad at the back to move independently; (2) it predisposes the pad to fold symmetrically, and contour to the buttocks; (3) it reduces the amount of material wedged in the buttocks crease; (4) it reduces the amount of material required in the pad; and (5) it reduces or eliminates the continuation of the structure created as the pad folds longitudinally when positioned and worn.

Figure 13:
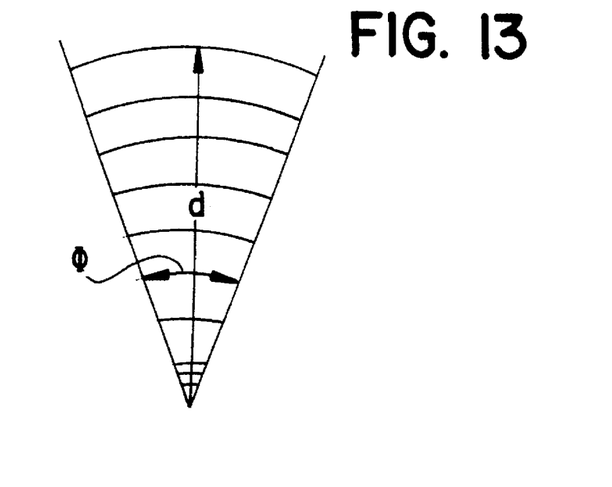
FIG. 13 illustrates the parameters describing the notches placed in the absorbent articles of this invention.
Figure 14:
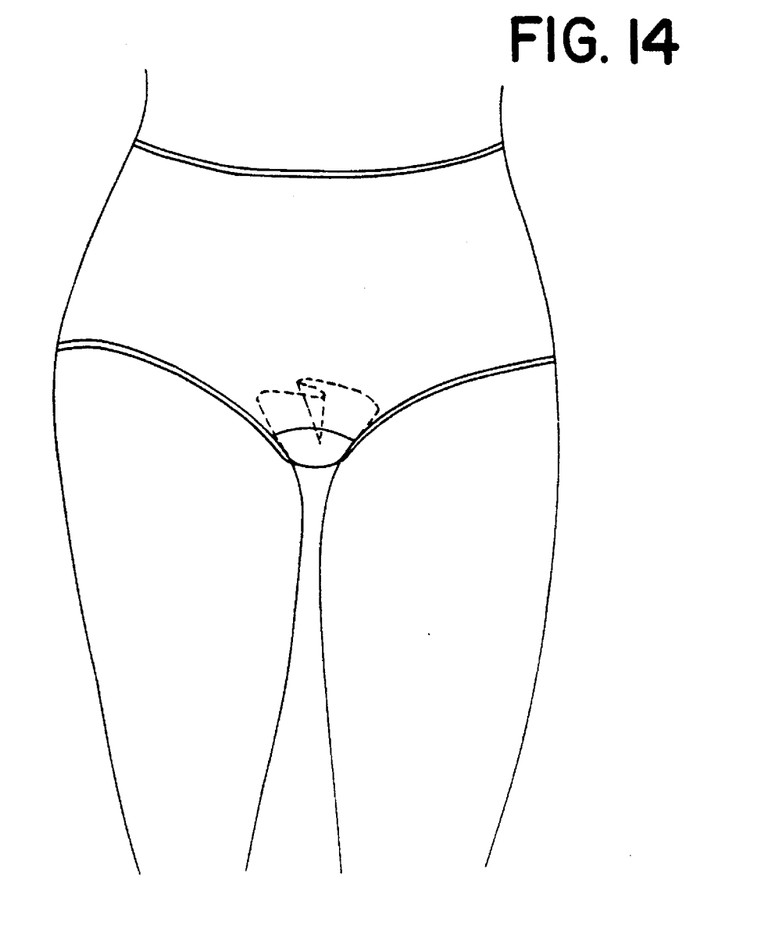
FIG. 14 is a front view of a sanitary napkin according to this invention placed in a panty on a wearer.
Figure 15A:
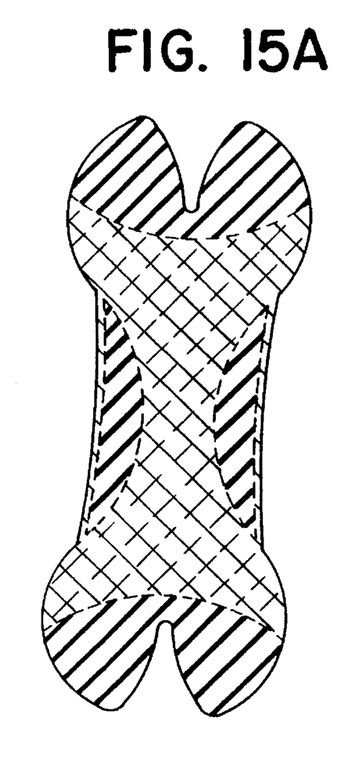
FIGS. 15A–C show a top plan view of a preferred embodiment of this invention.
Figure 15B:
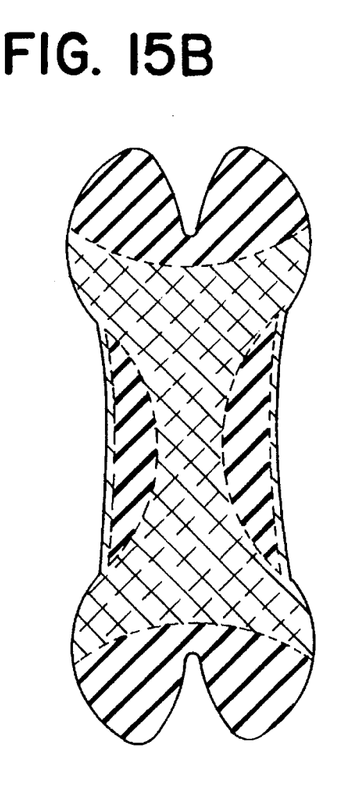
Figure 15C:
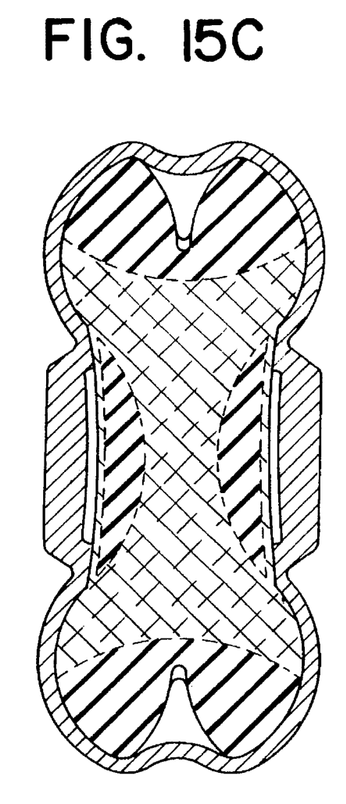

As is the case of the posterior portion, the front or anterior section of feminine hygiene pads must also conform to the curve of the perineal area. Clothing pulls up on pads, forming them into a cup shape. Since a two dimensional shape does not gracefully form a three-dimensional cup shape, pads pucker or fold unpredictably and ill-fittingly in the front. Typically, the pads pucker in the front, and either push themselves outward against the clothing or stick unevenly. This creates excess bulk, which is both uncomfortable and non-discrete. It can also cause the pad to shift out of the optimum position for capturing fluid. The designs disclosed above, when incorporated into the anterior end of a pad reduce the effects of uncontrolled puckering by removing material or controlling the behavior of materials in the appropriate areas, allowing the front of the pad to gather smoothly and such that it is discreet. The pad forms a graceful three-dimensional curve around the pubic curvature. An example of this is illustrated in FIG. 13, which shows a napkin according to this invention placed in a panty on a wearer. This figure illustrates the smooth conformability of the front-notched pad around the public bone area.

However, for any napkin design and combination of materials, there is a critical length for the notch, slit or stitched portion. The notch should not be extended so far into the pad that it causes the pad to fold away from the body. The width and number of the "V"s will vary depending on body size and materials properties. As explained above, the sides of the "V"s may arc outward in a scalloped fashion to form a more perfect seam as the cup shape is formed. The "V" cutout spaces may alternatively be bridged with thin, web-like fabric or film to provide additional control of the sides of the "V", especially where multiple "V"s are employed. Finally, the notches may be produced by embossing or stitching, or lined areas containing less material. Alternately, ruffles or pleats may be incorporated into the front, giving, in effect, the advantages of the "V" segment. These embodiments may be preferred in some cases for aesthetic reasons. Thinner material overall may supplement the effect.

However, whether formed in the anterior or posterior end of a pad the "V" segment is preferred because it offers several advantages. First, it reduces or eliminates the effects of the pad's structural longitudinal fold when worn. A fold otherwise allows the pad to push forward against the clothing, and be less discrete and less comfortable. Second, it reduces the amount of material required in the pad, reducing bulk. Third, it requires a simple die cut in manufacturing. Finally, it improves fit against the body, increasing comfort and stability.

Preferably, a foam backing should be used as opposed to a film backing. A foam backing generally exhibits more resiliency and structural stability than does a film backing.

Although certain embodiments of the present invention have been particularly described above, these are not meant to be limiting. Upon review of this specification, those of ordinary skill will realize that there are numerous adaptations, modifications and alternate embodiments that can be readily derived from this disclosure. Accordingly, in order to determine the true scope of the present invention, reference should be made to the appended claims.

What is claimed is:

1. An absorbent article comprising an absorbent core having a body-facing side and a garment-facing side an anterior end and a posterior end, the absorbent core comprised of:
   a bottom layer forming the garment-facing side and comprising cellulosic fibers and thermoplastic fibers, the bottom layer being embossed to form a pattern of areas of differing density; and
   an upper layer forming the body-facing side and comprised of cellulosic fibers and thermoplastic fibers;
   wherein at least one of the anterior and posterior ends comprises at least two identifiable portions divided by a modified portion.

2. The absorbent article of claim 1, wherein the bottom layer further comprises a superabsorbent material.

3. The absorbent article of claim 1, wherein the pattern of areas comprises a series of parallel lines of alternating densities.

4. The absorbent article of claim 1, wherein the pattern of areas comprises a series of intersecting lines of alternating densities.

5. The absorbent article of claim 1, wherein the pattern of areas comprises at least two sets of parallel lines that intersect to form a grid pattern of alternating densities.

6. The absorbent article of claim 1, further comprising a transfer layer disposed on the body facing side of the absorbent core.

7. The absorbent article of claim 1, wherein the top layer has a body facing surface and a longitudinal center line, the article further comprising a predetermined fold line formed in the body facing surface of the top layer.

8. The absorbent article of claim 1, in the form of a urinary incontinence pad.

9. The absorbent article of claim 1, in the form of a catamenial pad.

10. The absorbent article of claim 1, wherein the modified portion comprises an embossed line.

11. The absorbent article of claim 1, wherein the modified portion comprises a stitched line.

12. The absorbent article of claim 1, wherein the modified portion comprises a line of perforations.

13. The absorbent article of claim 1 further comprising an overwrap disposed on at least the body facing and garment facing sides of the absorbent core.

14. The absorbent article of claim 13, wherein the absorbent core has longitudinal side edges and the overwrap covers the longitudinal side edges.

15. The absorbent article of claim 1, wherein the modified portion comprises a V-shaped notch.

16. The absorbent article of claim 15, wherein one end of the absorbent layer comprises a plurality of V-shaped notches.

17. The absorbent article of claim 1 wherein the modified portion comprises a slit.

18. The absorbent article of claim 17 wherein one end of the absorbent layer comprises a plurality of slits.

19. The absorbent article of claim 1, wherein the modified portion comprises a scalloped notch.

20. The absorbent article of claim 19, wherein one end of the absorbent layer comprises a plurality of scalloped notches.

21. The absorbent article of claim 1, further comprising a facing disposed across the body facing side.

22. The absorbent article of claim 21, wherein the facing comprises a non-woven material.

23. The absorbent article of claim 22, wherein the non-woven material is comprised of thermoplastic fibers.

24. The absorbent article of claim 1, further comprising a backing sheet disposed across the garment facing side of the absorbent core.

25. The absorbent article of claim 24, wherein the backing sheet comprises a foam material.

26. The absorbent article of claim 25, wherein the foam material is thermoformed into a predetermined shape.

27. The absorbent article of claim 25, wherein the foam material is vacuum-formed into a predetermined shape.

28. The absorbent article of claim 25, wherein the absorbent core has longitudinal side edges, and wherein the foam material extends beyond the longitudinal side edges to form a gasketing edge.

29. A urinary incontinence pad comprising:
   an absorbent core having a body facing side, a garment facing side, an anterior end, and a posterior end, the absorbent core comprised of a bottom layer comprised of cellulosic fibers and thermoplastic fibers and a top layer comprised of cellulosic fibers and thermoplastic fibers, wherein the bottom layer is embossed to form a pattern of areas of differing density;
   a backing material disposed on the garment facing side of the absorbent core;
   a transfer layer disposed over at least a portion of the body facing side of the absorbent core;
   a cover layer disposed on the transfer layer substantially covering the body facing side of the absorbent core, wherein the cover layer is attached to the backing layer and a portion of at least one of the anterior and posterior ends has at least one notch.

30. The incontinence pad of claim 29, further comprising an overwrap layer disposed between the bottom layer and the backing layer.

31. The incontinence pad of claim 29, further comprising an overwrap layer disposed between the top layer and the bottom layer.

32. The incontinence pad of claim 29, wherein the absorbent core has longitudinal side edges and wherein the backing layer extends beyond the longitudinal side edges to form a gasketing edge.

33. The incontinence pad of claim 29, wherein the backing layer comprises a thermoformable foam material.

34. The incontinence pad of claim 29, wherein the backing layer comprises a non-thermoformable foam material.

35. The incontinence pad of claim 29, wherein the facing comprises a non-woven material comprised of thermoplastic fibers.

36. The incontinence pad of claim 29, wherein the transfer layer comprises a thermoplastic non-woven material.

37. The incontinence pad of claim 29, wherein the absorbent core has a longitudinal centerline and further comprising a longitudinal fold line formed in the absorbent core along the longitudinal centerline.

38. The incontinence pad of claim 37, wherein the longitudinal fold line is a slit cut through the absorbent core.

* * * * *